United States Patent [19]

Towle

[11] Patent Number: 4,841,011

[45] Date of Patent: * Jun. 20, 1989

[54] PREPARATION OF ARYLENE OLIGOMERS

[75] Inventor: Ian D. H. Towle, Cirencester, England

[73] Assignee: Raychem Limited, London, United Kingdom

[ * ] Notice: The portion of the term of this patent subsequent to Jun. 20, 2006 has been disclaimed.

[21] Appl. No.: 96,414

[22] Filed: Sep. 11, 1987

[30] Foreign Application Priority Data

Sep. 30, 1986 [GB] United Kingdom ............... 8623511

[51] Int. Cl.$^4$ .............. C08G 8/02; C08G 14/00
[52] U.S. Cl. .................... 528/125; 528/126; 528/128; 528/222; 528/223; 528/224; 528/225; 525/242; 525/280; 525/309
[58] Field of Search ............ 528/125, 126, 128, 222, 528/223, 224, 225; 525/242, 280, 309

[56] References Cited

U.S. PATENT DOCUMENTS

| | | | |
|---|---|---|---|
| 3,442,857 | 6/1969 | Thornton | 528/125 |
| 4,396,755 | 7/1983 | Rose | 528/126 |
| 4,698,393 | 10/1987 | Jansons et al. | 525/242 |
| 4,709,007 | 11/1987 | Jansons et al. | 528/222 |
| 4,721,771 | 1/1988 | Jansons et al. | 528/222 |

FOREIGN PATENT DOCUMENTS

| | | | |
|---|---|---|---|
| 1383393 | 2/1975 | United Kingdom | 528/125 |
| 2102420 | 2/1983 | United Kingdom . | |
| 2102442 | 2/1983 | United Kingdom . | |

OTHER PUBLICATIONS

Fieser & Fieser, *Advanced Organic Chemistry*, pp. 649–653 (Reinhold 1961).

*Primary Examiner*—Morton Foelak
*Assistant Examiner*—M. L. Moore
*Attorney, Agent, or Firm*—Yuan Chao; Edith A. Rice; Herbert G. Burkard

[57] ABSTRACT

Friedel Crafts preparation of arylene ether (especially arylene ether ketone) oligomers with an exceptionally high degree of isomeric purity and freedom from by-products can be achieved by adding to the Lewis acid reaction system a protic controlling agent selected from ROX, water, RCOOX, RSO$_3$X, and ROY, wherein R is organic, X is hydrogen or metal, and Y is metal.

Contrary to conventional expectation, the protic agent does not significantly acylate or alkylate the Friedel Crafts reaction product, and controlling agents of relatively low molecular weight, e.g., benzoic acid, can surprisingly be selected to produce dispersions of the resulting oligomers.

22 Claims, No Drawings

PREPARATION OF ARYLENE OLIGOMERS

This invention relates to a method of preparing arylene ketone oligomers and arylene sulphone oligomers and in particular to an electrophilic process for preparing such oligomers.

Arylene ketone and arylene sulphone oligomers, in particular arylene ether ketone oligomers are useful inter alia as so-called hard blocks in the preparation of di-, tri-or multi-segment block copolymers. When the number of segments is relatively small the hard blocks may contain as many as 100 repeat units, whilst for multi-segmented block copolymers the hard blocks may contain from 10-30 repeat units. They are also useful in the preparation of flame retardants, antioxidants and ultraviolet light stabilisers. This invention is directed to an improved electrophilic synthesis for preparing such oligomers, in particular para-linked oligomers.

In an electrophilic synthesis, the oligomerisation step involves the formation of an aryl ketone or sulphone group from a carboxylic or sulphonic acid or acid derivative group and an aromatic compound containing an aromatic carbon bearing an activated hydrogen atom, i.e., a hydrogen atom displaceable under the electrophilic reaction conditions. The monomer system employed in the polymerisation can be, for example, (a) a single aromatic compound containing both the acid or acid derivative group as well as an activated hydrogen atom on an aromatic carbon for example, p- phenoxybenzoyl chloride or p-phenoxysulphonlyl chloride; or (b) a two-component system of a dicarboxylic or disulphonic acid or acid derivative and an aromatic compound containing two activated hydrogen atoms, for example terephthaloyl chloride, and 1,4-diphenoxybenzophenone.

Electrophilic reactions of this type are referred to as Friedel-Crafts oligomerisation reactions. Typically, such oligomerisations are carried out in an anhydrous reaction medium comprising the reactant(s), a catalyst, such as anhydrous aluminium trichloride, and solvent such as methylene chloride, carbon disulfide, nitromethane, nitrobenzene, or ortho-dichlorobenzene, or mixtures thereof. Because the carbonyl or sulphonyl groups of the reactant(s) and products complex with aluminium trichloride and thereby deactivate it, the aluminium trichloride catalyst is generally employed in an amount greater than one equivalent for each equivalent of carbonyl or sulphonyl groups in the reaction medium. Other inorganic halides such as ferric chloride, may be employed as the catalyst.

Such Friedel-Crafts oligomerisations generally have tended to produce oligomer of poor thermal stability, relatively stable, all para-linked oligomers being particularly difficult to prepare under such Friedel-Crafts conditions. One factor that may lead to these poor results is that side reactions, particularly at the ortho position of activated aromatic rings, can result in a oligomer that is branched and/or is more likely to crosslink at elevated temperatures. It is generally recognized that in Friedel-Crafts reactions, ortho substitution is more likely to occur if the reaction is conducted at elevated temperatures and/or for a relatively long reaction time. U.S. Pat. Nos. 3,065,205; 3,767,620; 3,516,966; 3,791,890 and 4,008,203, and U.K. Pat. Nos. 971,227 and 1,086,021 disclose the preparation of poly(arylene ketones) by Friedel-Crafts polymerisation and generally acknowledge some of the difficulties in producing tractable, meltstable products.

To overcome these difficulties, it has been proposed to conduct Friedel-Crafts polymerisations using boron trifluoride catalyst in anhydrous hydrogen fluoride (see for example, U.S. Pat. Nos. 3,441,538; 3,442,857; 3,953,400 and 3,956,240). However, the use of boron trifluoride and hydrogen fluoride requires special techniques and equipment making this process difficult to practice on a commercial scale.

In European Published Patent Application No. 0178871 an electrophilic oligomerisation process is described which alleviates the disadvantages described above and does not require the special techniques and equipment necessary when boron trifluoride and hydrogen fluoride are used. In this method a Friedel-Crafts olgimerisation reaction is carried out under controlled or moderated conditions using a Lewis acid catalyst such as aluminium trichloride and a Lewis base as a controlling agent. This controlling agent generally maintains the oligomer in solution or in a swollen gel form in which polymerisation to the desired molecular weight can take place, and acts to suppress undesirable side reactions, particularly ortho substitution of the aromatic rings, so that an essentially linear oligomer is produced. Furthermore the process provides a high reaction rate which enables the reaction to be carried out at relatively low temperatures over a relatively short period of time.

One criterion for choosing the controlling agent in this process is that it should not be an acylating or alkylating agent, nor should it be acylatable under the reaction conditions. It is known that protic compounds act as acylating or alkylating agents in Friedel-Crafts reactions in the presence of aluminium trichloride.

However, it has now been surprisingly discovered that such compounds may be used as controlling agents in the process without themselves participating significantly in the acylation or alkylation reaction. Furthermore, it has been found that some of these controlling agent compounds will also act as dispersants to produce the oligomers in a conveniently dispersed state, despite the compounds preferably having fewer than the minimum of 8 aliphatic carbon atoms disclosed for long-chain dispersants for Friedel-Crafts polymerisations in European Published Patent Application No. 0174207. Appropriate long-chain dispersants of the Application No. 0174207, the disclosure of which is incorporated herein by reference, may also be used. Carboxylic acids, e.g. succinic acid and benzoic acid, have proved particularly useful in this respect. It cannot be reliably predicted whether a particular controlling agent will act as a dipersant, since this appears to depend on the other materials present and their relative properties and reaction conditions, but the dispersant effect is readily recognised (and reproduced once recognised) by suitably skilled operators. It has also been discovered that water can be added as the controlling agent, contrary to the well-known requirement for substantially anhydrous conditions in Friedel-Crafts reactions.

Accordingly the present invention provides in one aspect a method of preparing an arylene oligomer having the repeat unit:

-Ar-O-Ar-B- where each B independently is a carbonyl (—CO—) or sulphonyl (—SO$_2$—) group, and each Ar is independently a substituted or unsubstituted phenylene moiety or a substituted or unsubstituted polynuclear moiety, aromatic carbon atoms of which are bonded directly to the —O— or —CO— or —SO$_2$— groups,
which comprises oligomerising a monomer system comprising (I) phosgene or an aromatic or aliphatic carboxylic or sulphonic diacid dihalide monomer and a polynuclear aromatic comonomer having two activated hydrogens or (II) a self-oligomerising polynuclear aromatic monomer containing both a carboxylic or sulphonic acid halide group and an active hydrogen atom, in a reaction medium comprising:

(A) a Lewis acid;
(B) a controlling agent comprising:
  (i) R(OX)$_a$ or added water which must be present in the reaction medium together with the Lewis acid before any monomer containing acid halide groups is added,
  (ii) R(COOX)$_a$,
  (iii) R(SO$_3$X)$_a$, or
  (iv) (RO)$_b$Y, which, if the Y—O linkage(s) are reactive to acid halide groups, must be present in the reaction medium together with the Lewis acid before any monomer containing acid halide groups is added,
  where R is a monovalent or polyvalent organic group compatible with the monomer(s) and the other components of the reaction medium,
  each X independently is a hydrogen atom or a monovalent metal atom,
  each a independently is 1 or 2,
  Y is a multivalent metal atom, and
  b is an integer equal to the valency of Y; and
(C) optionally a non-protic diluent;

the various components being present in such proportions and the oligomerisation being conducted under such reaction conditions that a substantially linear arylene oligomer substantially free of pendant groups resulting from ortho substitution of para-linked aromatic rings in the oligomer backbone is obtained either in a dispersed state, in which case the group R of the controlling agent (B) preferably has fewer than 8 aliphatic carbon atoms directly bonded to one another, or in a solution or gel state.

In a second aspect the present invention provides a method of producing an arylene oligomer which comprises oligomerising a monomer system comprising:

(I) (i) phosgene or an aromatic or aliphatic carboxylic or sulphonic diacid dihalide monomer and:
  (ii) a polynuclear aromatic comonomer comprising:
    (a) H-Ar-O-Ar-H
    (b) H-(Ar-O)$_n$-Ar-H wherein n is 2 or 3
    (c) H-Ar-O-Ar-(B-Ar-O-$^{Ar}$)$_m$-H wherein m is 1, 2 or 3 or
    (d) H-(Ar-O)$_n$-Ar-B-Ar-(O-Ar)$_m$-H wherein m is 1, 2, or 3, and n is 2 or 3 or
(II) a self-oligomerising carboxylic or sulphonic acid halide monomer of the formula
H-Ar-O-[(Ar-B)$_p$-(O-Ar)$_q$-(Ar-B)$_r$]$_k$-Ar-B-Z wherein Z is halogen, k is 0, 1 or 2, p is 1 or 2, q is 0, 1 or 2 and r is 0, 1 or 2; or
(III) a self-oligomerising carboxylic or sulphonic acid halide monomer of the formula:
H-(Ar-O)$_n$-Ar-Y wherein n is 2 or 3 and Y is B-Z or B-Ar-B-Z;
where Z is halogen;
wherein each B independently is a carbonyl (-CO-) or sulphonyl (-SO$_2$-) group, and each Ar is independently selected from substituted or unsubstituted phenylene, and substituted and unsubstituted polynuclear aromatic moieties the end one of the aromatic moieties being activated to electrophilic attack e.g. by an ether linkage to the next moiety;

in a reaction medium comprising (A) a Lewis acid in an amount of about one equivalent per equivalent of carbonyl or sulphonyl groups present in the monomer system plus about one equivalent per equivalent of controlling agent, plus an amount effective to act as a catalyst for the oligomerisation;
(B) a controlling agent, in an amount from 0.25 to 4 equivalents per equivalent of acid halide groups present in the monomer system, comprising:
  (i) R(OX)$_a$ or added water which must be present in the reaction medium together with the Lewis acid before any monomer containing acid halide group is added,
  (ii) R(COOX)$_a$,
  (iii) R(SO$_3$X)$_a$, or
  (iv) (RO)$_b$Y, which, if the Y-O linkage(s) are reactive to acid halide groups, must be present in the reaction medium together with the Lewis acid before any monomer containing acid halide groups is added,
  where R is an organic group compatible with the monomer(s) and the other components of the reaction medium and, when the oligomer is produced in a dispersed state, preferably has fewer than 8 aliphatic carbon atoms directly bonded to one another,
  each X independently is a hydrogen atom or a monovalent metal atom,
  each a independently is 1 or 2,
  Y is a multivalent metal atom; and
  b is an integer equal to the valency of Y; and
(C) a non-protic diluent in an amount from 0 to about 93% by weight, based on the weight of the total reaction mixture.

Thus the process of the present invention enables substanitally linear arylene oligomers to be prepared using as a controlling agent a generally cheap and easily available compound (or compounds) which is relatively non-hazardous. This invention is especially concerned with preparation of the aromatic oligomers having an inherent viscosity of less than about 0.6 and having at least 2 repeat units. Throughout this application, inherent viscosity refers to the mean inherent viscosity determined according to the method of Sorenson et al, "Preparative Methods of Oligomer Chemistry" Intersience (1986), at page 44 [0.2 g oligomer dissolved in 100 ml of concentrated sulfuric acid at 25° C.].

It will be redily understood that the group R in the controlling agent (B) is compatible with the monomer(s) and the other components of the reaction medium in the sense that it does not unacceptably interfere with the reaction. Provided that is so, R may be any desired monofunctional or (where appropriate) difunctional aliphatic aromatic or heterocyclic group, for example, a substituted or unsubstituted alkyl, alkylene, aryl, arylene, alkaryl or aralkyl group. Simple aliphatic or aromatic groups are preferred, especially alkyl and alkylene groups, preferably n-alkyl and n-alkylene groups, and phenyl or naphthyl groups or phenylene or naphthylene groups.

Where the controlling agent is of the formula $R(OX)_a$ as defined above, the controlling agent may be an alcohol ROH, which also includes diols HOROH, or an organic metal oxide where X is, for example, an alkali metal such as sodium. In view of their strong affinity for reaction with acid halide groups, it is surprising that alcohols can be used as the controlling agent, even with the specified order of addition to the reaction mixture, which unexpectedly prevents reaction with the acid halide. Unbranched alcohols, e.g. n-alkanols, are preferred, especially the n-lower alkanols, e.g. n-butanol.

Where the controlling agent is of the formula $R(COOX)_a$ as defined above, this may be a carboxylic acid R—COOH, which includes dicarboxylic acids XOOC—R—COOX, or metal salts thereof where X is, for example an alkali metal.

Where the controlling agnet is of the formula $(R-O)_b$ Y, Y is preferably a di- or trivalent metal atom and b is 2, 3 or 4 respectively e.g. $(RO)_3Al$, $(RO)_4Ti$, $(RO)_2Zn$.

Preferably R is a substituted or unsubstituted aryl group, or linear or branched alky group, or their arylene or alkylene equivalents where appropriate. More preferably R is an unsubstituted alkyl group especially a $C_1$-$C_5$ alkyl group, e.g. a methyl, ethyl, propyl, isopropyl, n-butyl or isobutyl group; or an unsubstituted aryl group, e.g. a phenyl or naphthyl group, and preferably aryl R groups are deactivated to electrophilic attack by attachment of electron-withdrawing groups.

It is also preferred that the controlling agents have fewer than 8 aliphatic carbon atoms, or even fewer than 5 aliphatic carbon atoms, directly bonded to one another, this including the possibilities that only one or no aliphatic carbon atoms are present, or that fewer than the stated numbers of such atoms are present in any one group, in the controlling agent molecule.

More specific examples of suitable controlling agents include methanol, ethanol, isopropanol, butanol, acetic acid, propionic acid, butanoic acid, trichloroacetic acid, trifluoroacetic acid, methane sulphonic acid, succinic acid, sodium methoxide, sodium ethoxide, $(CH_3CH_2O)_3Al$, $(CH_3COO)_3Al$, pentafluorophenol, and benzoic acid. It appears that trifluoroacetic acid may have the useful ability to produce a very fast reaction, or alternatively to reduce the amount of aluminium chloride needed for a given reaction speed possibly because the electron-withdrawing effect of the fluroine atoms produces a more highly charged aluminium atom in the resulting Lewis acid/controlling agent complex.

Mixtures of two or more controlling agents may be used if desired, and mixtures of the present protic controlling agent(s) with the non-protic Lewis base controlling agents described in the aforementioned European Patent Application No. 0124276 (whose disclosure is incorporated herein by reference) may be helpful. Methanol controlling agent plus sulpholane Lewis base is one example of such a mixture.

As mentioned above, the controlling agent acts, inter alia, to suppress undesirable side reactions, particularly ortho substitution of the aromatic rings in the monomer system. It is believed that the aromatic rings which are particularly susceptible to ortho substitution are active aryloxy groups. Such groups are referred to herein as undeactivated aryloxy groups. By "undeactivated aryloxy group" is meant an aryloxy group which is in a molecule in which there are no deactivating groups or is located at least two aromatic moieties (i.e. Ar as defined above) away from a deactivating group such as a carbonyl. Conversely a "deactivated aryloxy group" is an aryloxy group separated from a deactivating group, usually carbonyl, by an aromatic group containing one aromatic ring, fused aromatic rings or aromatic rings linked by direct bonds. Suppression of side reactions results in a oligomer that is thermally stable, that is it does not degrade or cross-link when subjected to elevated temperatures, for a period of time. For an oligomer of this type to be suitable for melt processing, it must be able to withstand the processing temperatures for the required processing time. Typically these conditions require that the oligomer can withstand temperatures up to about 30° C. above the melting or softening point of the oligomer for periods of at least 30 minutes, preferably at least 60 minutes and most preferably at least 90 minutes, without undesired gel formation or substantial change in inherent viscosity. However, in many cases, heat-reactive oligomers will be desirable for further reaction in their subsequent uses.

The amount of controlling agent present is preferably from 0.1 to 4 equivalents per equivalent of acid halide groups present in the monomer system. Amounts greater than 4 equivalents could be employed, if desired. However, no additional controlling effect is usually achieved by adding larger amounts. Thus, it is preferred to use no more than 4 equivalents, more preferably between 0.5 and 4 equivalents and especially between 0.5 and 2 equivalents per equivalent of acid halide groups. The actual amount of controlling agent added depends upon, inter alia, the particular controlling agent used, the nature of the monomers present and the type and amount of Lewis acid employed.

While it is not understood exactly how the controlling agent acts to control the reaction, it is believed that one or more of the following factors may be involved. It is thought that the controlling agent forms a complex or compound (hereinafter "complex" for simplicity) with the Lewis acid. The complex appears to act as a solvent for the oligomer-Lewis acid complex formed during the reaction thereby maintaining the oligomer in solution or in a reactive gel state and in some cases producing a dispersion of the resulting oligomer. Further, the reaction mixture is more tractable, making work up of the oligomer easier and ensuring effective removal of catalyst residues during purification. The solubilization property of the Lewis acid/controlling agent is particularly significant in the preparation of para-linked arylene ether ketone oligomers. Thus, in accordance with the invention, the controlling agent is selected such that, usually in complex form with the Lewis acid, it maintains the resulting oligomer in solution, at least until a desired molecular weight is reached, and may conveniently produce a dispersion of the oligomer. Whether a controlling agent will maintain the eventual oligomer in solution/gel or disperse it can be readily determined by experiment.

The term "Lewis acid" is used herein to refer to a substance which can accept an unshared electron pair from another molecule. Lewis acids which can be used in the practice of this invention include, for example, aluminum trichloride, aluminum tribromide, antimony pentachloride, antimony pentafluoride, indiuim trichloride, gallium trichloride, boron trichloride, boron trifluoride, zinc chloride, ferric chloride, stannic chloride, titanium tetrachloride, and molybdenum pentachloride. The use of substantially anhydrous aluminum trichloride as the Lewis acid is preferred.

The amount of Lewis acid used in the practice of this invention varies depending on the particular monomers and reaction medium selected. In all instances at least about one quivalent of Lewis acid per equivalent of carbonyl groups present in the monomer system is used plus one equivalent per equivalent of controlling agent used plus an amount effective to act as a catalyst for the polymerisation (also referred to herein as a catalytic amount). Generally a catalytic amount added is from about 0.05 to about 0.5 equivalents of Lewis acid per equivalent of acid halide in the reaction mixture. When aluminium chloride is used as the Lewis acid one equivalent is considered to be $AlCl_3$. Further, if a comonomer containing other basic species, such as sulfone groups, is used, additional Lewis acid may be required.

A non-protic diluent can also be employed, if desired, "non-protic" meaning that the diluent has no hydrogens directly bonded to oxygen or nitrogen. Such diluents are also known as "aprotic". Advantageously, the diluent should dissolve the Lewis acid/controlling agent complex and the resulting oligomer/Lewis acid complex. It should also be relatively inert toward Friedel-Crafts reactions. The diluent is preferably somewhat polar as measured by its dielectric constant and solubility parameter. Preferably the dielectric constant of the diluent is at least about 2.0 at 24° C., and preferably in the range of from about 4.0 to about 25 at 24° C. The Hildebrand solubility parameter of the diluent is preferably at least about 7.2 $[cal/cm^3]^{\frac{1}{2}}$ and is preferably in the range of from about 9.2 to about 15 $[cal/cm^3]^{\frac{1}{2}}$. Preferred diluents include, for example, methylene chloride, carbon disulfide, o-dichlorobenzene, 1,2,4-trichlorobenzene, o-difluorobenzene, 1,2,-dichloroethane, cyclohexane, 1,1,2,2,-tetrachloroethane and mixtures thereof.

The diluent is used in an amount from 0 to about 93% by weight, based on the weight of the total reaction mixture. The reactions can be run without the presence of a diluent. Typically the diluent is used in an amount of at least about 10%, preferably at least about 20% by weight of the reaction mixtures.

"Arylene ketone" oligomers contain arylene and ketone groups and may also contain additional groups in the oligomer chain, including, for example, ether, sulfone, sulfide, amide, imide, azo, alkylene, perfluoroalkylene and other appropriate groups. Similarly, "arylene sulfone" oligomers contain arylene and sulfone groups in the oligomer optionally with other linkages.

Generally, the monomer system comprises: (a) an aromatic compound containing a carboxylic or sulfonic acid derivative and an active hydrogen atom being activated toward electrophilic displacement by, for example, an electron donating group situated ortho or para with respect to said hydrogen atom; or (b) a two-monomer system of a dicarboxylic or disulfonic acid derivative group and an aromatic compound containing two such displaceable active hydrogen atoms. The term "active hydrogen atom" refers to a hydrogen atom bound to an aromatic carbon atom, i.e. a carbon atom which is part of an aromatic ring.

In defining the monomer system, the term polynuclear aromatic moieties is used to mean aromatic moieties containing at least two aromatic rings. The rings can be fused, joined by a direct bond or by a linking group. In certain monomers, at least two of the aromatic rings are linked by an ether oxygen linkage. Other linking groups which can join aromatic rings in the aromatic moieties include for example, ether, carbonyl, sulfone, sulfide, amide, imide, azo, alkylene, perfluoroalkylene and the like.

The phenylene and polynuclear aromatic moieties contained in the monomers can contain substitutents on the aromatic rings. Such substitutents should not inhibit or otherwise interfere with the polymerisation reaction to any significant extent. Such acceptable substitutents include, for example, phenyl, halogen, ester, nitro, cyano, alkyl and the like.

Where an aromatic diacid dihalide is employed, it is preferably a dichloride or dibromide. Examples of suitable diacid dihalide monomers, polynuclear aromatic comonomers which can be used with such diacid dihalide monomers, and self-polymerising acid halide monomers are described in the aforementioned European Published Patent Application No. 0178871, the disclosure of which is incorporated herein by reference.

It is to be understood that combinations of monomers can be employed. For example, one or more diacid dihalides can be used with one or more polynuclear aromatic comonomers as long as the correct stoichiometry is maintained. Further, one or more acid halides can be included. In addition monomers which do not contain an ether linkage can be employed as long as one or more of the monomers used contains at least one ether oxygen linkage, for example Ph-O-Ph-$SO_2$-Ph-O-Ph, or Ph-O-Ph-C($CH_3$)$_2$-Ph-O-Ph, wherein Ph represents a p-phenylene unit, which can be used as the sole monomer with an ether containing diacid dihalide or with phosgene or any diacid dihalide when used in addition to a polynuclear aromatic monomer.

If desired, the molecular weight of the oligomer, the degree of branching and amount of gelation can be controlled by the use of, for example, capping agents as described in U.S. Pat. No. 4,247,682, the disclosure of which is incorporated herein by reference. The molecular weight of the oligomer can also be controlled in a reaction utilizing a two-monomer system as described above, by employing a slight excess of one of the monomers.

The temperature at which the reaction is conducted can be from about −50° C. to about +150° C. It is peferred to start the reaction at lower temperatures, for example at about −50° C. to about −10° C. particularly if the monomer system contains highly reactive monomers. After reaction has commenced, the temperature can be raised if desired, for example, to increase the rate of reaction. It is generally preferred to carry out the reaction at temperature in the range of between about −30°C and +25° C.

Capping agents, when employed, are added to the reaction medium to cap the oligomer on at least one end of the oligomer chain. This terminates continued growth of that chain and controls the resulting molecular weight of the oligomer, as shown by the inherent viscosity of the oligomer. Judicious use of the capping agents results in a oligomer within a selected narrow molecular weight range, decreased gel formation during oligomerisation, and decreased branching of the oligomer chains and increases oligomer stability. Both nucleophilic and electrophilic capping agents may be used to cap the oligomer at each end of the chain.

Preferred nucleophilic capping agents are 4-chlorobiphenyl, 4-phenoxybenzophenone, 4-(4-phenoxy-phenoxy)benzophenone, biphenyl 4-benzenesulphonylphenyl phenyl ether, and the like.

Typical electrophilic capping agents are compounds of the formula

Ar-CO-E or Ar-SO$_2$-E wherein Ar" is phenyl, 3-chlorophenyl, 4-chlorophenyl, 4-cyanophenyl, 4-methylphenyl or an aromatic group substituted with an electron withdrawing substitutent and E is halogen or other leaving group. Preferred electrophilic capping agents include benzoyl chloride, benzenesulfonyl chloride and the like.

As mentioned above, a key aspect of this invention is that the Lewis acid/controlling agent complex apparently solubilizes or solvates the oligomer so that it remains in the reaction medium in a form capable of sustaining reaction to the desired molecular weight in a controlled and reproducible fashion either as a solution/gel or as a dispersion. Lewis acid is also present in the reaction medium as the catalyst for the Friedel-Crafts polymerisation reaction. The resulting oligomer contains Lewis acid complexed to the carbonyl groups of the oligomer. In many cases, the Lewis acid is complexed to substantially all the carbonyl groups in the oligomer, and this catalyst residue must be removed, i.e. the Lewis acid must be decomplexed from the oligomer and removed. A method for removing the catalyst residue is described in U.S. Patent No. 4,237,884 the disclosure of which is incorporated herein by reference.

Decomplexation can be accomplished by treating the polymerisation reaction mixture with a decomplexing base after completion of polymerisation. The base can be added to the reaction medium or the reaction medium can be added to the base. The decomplexing base must be at least as basic towards the Lewis acid as the basic groups on the oligomer chain. Such decomplexation should be effected before isolation of the oligomer from the reaction mixture.

The amount of decomplexing base used should be in excess of the total amount of bound (complexed) and unbound Lewis acid present in the reaction mixture and is preferably at least twice the total amount of Lewis acid. Typical decomplexing bases which can be used include water, dilute aqueous hydrochloric acid, methanol, ethanol, acetone, N,N-dimethyl-formamide, N,N-dimethylacetamide, pyridine, dimethyl ether, diethyl ether, tetrahydrofuran, trimethylamine hydrochloride, dimethyl sulfide, tetramethylenesulfone, benzophenone, tetramethylammonium chloride, isopropanol and the like. The decomplexed oligomer can then be removed by conventional techniques such as adding a nonsolvent for the oligomer which is a solvent for or miscible with the Lewis acid/controlling agent complex and Lewis acid; spraying the reaction medium into a nonsolvent for the oligomer; separating the oligomer by filtration; or evaporating the volatiles from the reaction medium and then washing with an appropriate solvent to remove any remaining complex and diluent from the oligomer.

The ivention is further illustrated by the following specific examples.

EXAMPLE 1

(In all examples Ph represents a paraphenylene unit)

Preparation of the Oligomer

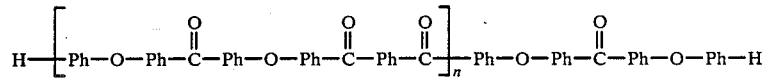

To a 250 ml flask equipped with a stirrer and nitrogen inlet was added 100 mls of dichloromethane. After cooling the contents to $-25°$ C. 20.51 g (0.154 M) of anhydrous aluminium chloride was added. After cooling the contents back to $-25°$ C. 3.7 g (0.05 M) of n-butanol was added at a rate such that the temperature of the contents of the flask did not rise above $-15°$ C. This was followed by the addition at $-20°$ C., of 10.8290 g (0.02955 M) of 4,4'-diphenoxybenzophenone which was rinsed into the flask with 25 mls of dichloromethane. Finally 5.00 g (0.02463 M) of terephthaloyl chloride was added to the flask and rinsed in with 25 mls of dichloromethane. The temperature of the reaction was then allowed to rise to room temperature (20° C.) and maintained for 6 hours. After this time the reaction mixture was poured with stirring into 500 mls of 4N HCl that had been prepared using ice ($-18°$ C.). The oligomer was allowed to decomplex overnight. After replacing the decomplexing mixture with fresh 4N HCl the volatile organics were removed using a Dean-Stark head, by bringing the acid suspension to reflux. After 4 hours the acid was replaced by de-ionized water and this was also refluxed for 4 hours, and then repeated. Any traces of acid were then neutralised by boiling in pH 10 aqueous ammonia for 4 hours. Finally the oligomer was filtered off and washed with four portions of hot (85° C.) de-ionised water with slurring. The oligomer was dried at 150° C. in a vacuum oven.

The phenoxy terminated structure above was confirmed by $^{13}C$ and $^1H$ n.m.r. spectroscopy, no acid end groups were detected.

The I.V. of the material measured as a 0.2% solution in 98% sulphuric acid was 0.24 dl/g.

The above procedure was repeated using benzoic acid 6.1 g (0.05 M), acetic acid 3 g (0.05 M) and trifluoroacetic acid 5.7 g (0.05 M) in place of butanol.

Where as with butanol a solution of the oligomer was obtained, dispersions were obtained with benzoic acid and trifluoroacetic acid and a gel obtained with acetic acid.

| Example | Modifier | Reaction Appearance | I.V. dl/g |
|---------|----------|---------------------|-----------|
| 1 | Butanol | Solution | 0.24 |
| 2 | Benzoic Acid | Dispersion | 0.28 |
| 3 | CF$_3$COOH | Dispersion | 0.25 |
| 4 | Acetic Acid | Gel | 0.28 |

EXAMPLE 2

Preparation of the Oligomer

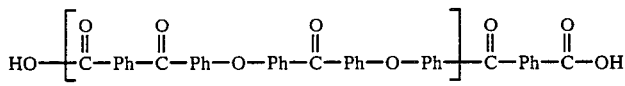

Using the procedure outlined in Example 1 the above oligomer was prepared using the reagents specified below.

| | | |
|---|---|---|
| 4,4'-Diphenoxybensophenone | 9.02 g | 0.02463 Mols |
| Terephthaloyl chloride | 6.0 g | 0.02955 Mols |
| Aluminium chloride | 20.51 g | 0.1538 Mols |
| Benzoic acid | 6.1 g | (0.05 M Mols) |
| Dichloromethane | 100 mls | |

The resultant oligomer had an inherent viscosity of

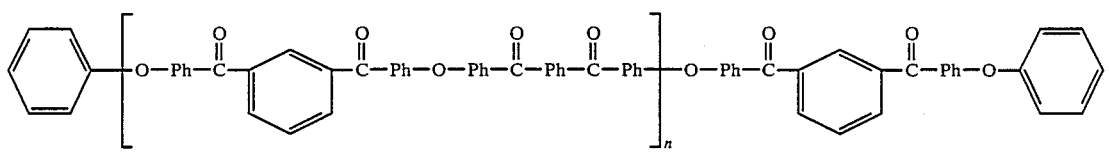

0.26 dl/g as measured in a 0.2% solution in 98% sulphuric acid. The structure of the oligomer was confirmed by $^{13}C$ n.m.r. spectroscopy.

EXAMPLE 3
Preparation of the oligomer

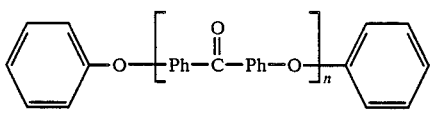

To a 250 ml reaction flask, equipped with a stirrer and having been purged with nitrogen was added 100 mls of dichloromethane. After cooling to −25° C. 28.5 g (0.214 Mols) of anhydrous aluminium chloride was added. After allowing the slurry to cool back to −25° C. 3.18 g (0.043 Mols) of n-butanol was added at a rate such that the temperature in the flask did not rise above −15° C. After allowing the mixture to cool back to −20° C 20 g (0.086 Mols) of p-phenoxybenzoylchloride was added, keeping the temperature below −15° C., and washed into the flask with 20 mls of dichloromethane. After the addition was complete the temperature of the mixture was raised to +5° C. and during this time 0.6302 g (1.72×10⁻³ Mols) of 4,4'-diphenoxybenzophenone was added to the reaction flask and washed in with 10 mls of dichloromethane. The reaction was maintained at +5° C. for 16 hours.

The oligomer was isolated using the method outlined in Example 1.

The oligomer thus obtained had an inherent viscosity of 0.36 dl/g as measured in a 0.2% solution of 98% sulphuric acid. The structure of the oligomer was confirmed by $^{13}C$ n.m.r. spectroscopy.

EXAMPLE 4
Preparation of the oligomer

Using the procedure outlined in Example 1 the above oligomer was prepared using the reagents specified below.

| | | |
|---|---|---|
| 1,3-Bis(4-phenoxybenzoyl)benzene | 27.81 g | (0.05910 Mols) |
| Terephthaloyl chloride | 10 g | (0.04925 Mols) |
| Aluminium chloride | 36.00 g | (0.27 Mols) |
| Butanol | 7.4 g | (0.1 Mols) |
| Dichloromethane | 100 mls | |

The resultant oligomer had an inherent viscosity of 0.32 dl/g as measured in a 0.2% solution in 98% sulphuric acid.

An oligomer containing the unit

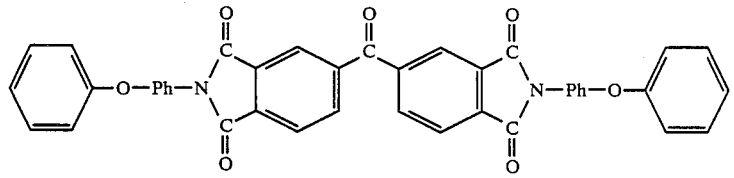

instead of the first reagent listed was similarly prepared.

EXAMPLE 5
Preparation of the oligomer

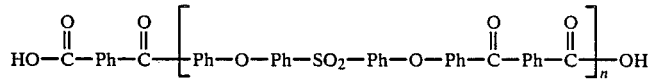

Using the procedure outlined in Example 1 the above oligomer was prepared using the reagents specified below.

| | | |
|---|---|---|
| 4,4'-Diphenoxydiphenylsulphone | 23.78 g | (0.05910 Mols) |
| Terephthaloyl chloride | 10 g | (0.04925 Mols) |
| Aluminium chloride | 33.33 g | (0.25 Mols) |
| Benzoic acid | 3.05 g | (0.025 Mols) |
| Dimethyl sulphone | 2.35 g | (0.025 Mols) |

| | |
|---|---|
| -continued | |
| Dichloromethane | 100 mls |

The resultant oligomer had an inherent viscosity of 0.23 dl/g as measured in a 0.2% solution in 98% sulphuric acid.

The structure of the oligomer was confirmed by $^{13}C$ n.m.r. spectroscopy.

I claim:

1. A method of preparing an arylene oligomer having the repeat unit:
ti -Ar-O-Ar-B- where
each B independently is a carbonyl (—CO—) or sulphonyl (—SO$_2$—) group, and each Ar is independently a substituted or unsubstituted phenylene moiety or a substituted or unsubstituted polynuclear moiety, aromatic carbon atoms of which are bonded directly to the —O— or —CO— or SO$_2$ groups,
which comprises oligomerising a monomer system comprising (I) phosgene or an aromatic or aliphatic carboxylic or sulphonic diacid dihalide monomer and a polynuclear aromatic comonomer having two activated hydrogens or (II) a self-oligomerising polynuclear aromatic monomer containing both a carboxylic or sulphonic acid halide group and an active hydrogen atom, in a reaction medium comprising:
(A) a Lewis acid;
(B) a controlling agent comprising:
(i) $R(OX)_a$ or added water which must be present in the reaction medium together with the Lewis acid before any monomer containing acid halide groups is added,
(ii) $R(COOX)_a$,
(iii) $R(SO_3X)_a$, or
(iv) $(RO)_b Y$, which, if the Y-O linkage(s) are reactive to acid halide groups, must be present in the reaction medium together with the Lewis acid before any monomer containing acid halide groups is added,
where R is a monovalent or polyvalent organic group compatible with the monomer(s) and the other components of the reaction medium,
each X independently is a hydrogen atom or a monovalent metal atom,
each a independently is 1 or 2,
Y is a multivalent metal atom, and
b is an integer equal to the valency of Y; and
(C) optionally a non-protic diluent;
the various components being present in such proportions and the oligomerisation being conducted under such reaction conditions that a substantially linear arylene oligomer substantially free of pendant groups resulting from ortho substitution of para-linked aromatic rings in the oligomer back-bone is obtained either in a dispersed state, in which case the group R of the controlling agent (B) preferably has fewer than 8 aliphatic carbon atoms directly bonded to one another, or in a solution or gel state.

2. A method of producing an arylene oligomer which comprises oligomerising a monomer system comprising:
(I)
(i) phosgene or an aromatic or aliphatic carboxylic or sulphonic diacid dihalide monomer and:
(ii) a polynuclear aromatic comonomer comprising:
(a) H-Ar-O-Ar-H
(b) H-(Ar-O)$_n$-Ar-H wherein n is 2 or 3
(c) H-Ar-O-Ar-(B-Ar-O$^{Ar}$)$_m$-H wherein m is 1, 2 or 3 or
(d) H-(Ar-O)$_n$-Ar-B-Ar-(O-Ar)$_m$-H wherein m is 1, 2, or 3, and
n is 2 or 3 or
(II)
a self-oligomerising carboxylic or sulphonic acid halide monomer of the formula
H-Ar-O-[(Ar-B)$_p$-(O-Ar)$_q$-(Ar-B)$_r$]$_k$-Ar-B-Z
wherein Z is halogen, k is 0, 1 or 2, p is 1 or 2, q is 0, 1 or 2 and r is 0, 1 or 2; or
(III)
a self-oligomerising carboxylic or sulphonic acid halide monomer the formula:
H-(Ar-O)$_n$-Ar-Y wherein n is 2 or 3 and Y is B-Z or B-Ar-B-Z;
where Z is halogen;
wherein each B independently is a carbonyl (-CO-) or sulphonyl (—SO$_2$) group, and each Ar is independently selected from substituted or unsubstituted phenylene, and substituted and unsubstituted polynuclear aromatic moieties;
in a reaction medium comprising
(A) a Lewis acid in an amount of about one equivalent per equivalent of carbonyl or sulphonyl groups present in the monomer system plus about one equivalent per equivalent of controlling agent, plus an amount effective to act as a catalyst for the oligomerisation;
(B) a controlling agent, in an amount from 0.25 to 4 equivalents per equivalent of acid halide groups present in the monomer system, comprising:
(i) $R(OX)_a$ or added water which must be present in the reaction medium together with the Lewis acid before any monomer containing acid halide group is added,
(ii) $R(COOX)_a$,
(iii) $R(SO_3X)_a$, or
(iv) $(RO)_b Y$, which, if the Y-O linkage(s) are reactive to acid halide groups, must be present in the reaction medium together with the Lewis acid before any monomer containing acid halide groups is added,
where R is an organic group compatible with with the monomer(s) and the other components of the reaction medium and, when the oligomer is produced in a dispersed state, preferably has fewer then 8 aliphatic carbon atoms directly bonded to one another,
each X independently is a hydrogen atom or atom or a monovalent metal atom,
each a independently is 1 or 2,
Y is a multivalent metal atom; and
b is an integer equal to the valency
of Y; and
(C) a non-protic diluent in an amount from 0 to about 93% by weight, based on the
weight of the total reaction mixture.

3. A method according to claim 1 or 2 wherein the controlling agent is an alcohol, carboxylic acid or organic metal oxide.

4. A method according to claim 1 or 2 wherein R is an alkyl group.

5. A method according to claim 1 or 2, wherein the controlling agent is an n-alkanol.

6. A method according to claim 1 or 2, wherein R is an aryl group.

7. A method according to claim 1 or 2, wherein the controlling agent is an aryl carboxylic acid.

8. A method according to claim 1 or 2, wherein the controlling agent molecule contains fewer than 8 aliphatic carbon atoms directly bonded to one another.

9. A method according to claim 1 or 2, wherein the amount of controlling agent present in the reaction medium is between 0.1 and 4 equivalents per equivalent of acid halide groups present in the monomer system.

10. A method according to claim 1 or 2, wherein the Lewis acid is selected from aluminium trichloride, boron trichloride, aluminium tribromide, titanium tetrachloride, antimony pentachloride, ferric chloride, gallium trichloride, and molybdenum penta-chloride.

11. A method according to claim 1 or 2, wherein the Lewis acid is aluminium trichloride.

12. A method according to claim 1 or 2, wherein said polymerisation is carried out in the pre-sence of a non-protic dilutent.

13. A method according to claim 1 or 2, wherein said polymerisation is carried out in the presence of a non-protic diluent having a dielectric constant of at least 2.0 preferably from 4.0 to 25, at 24° C.

14. A method according to claim 1 or 2, wherein the monomer system comprises p-phenoxybenzoyl chloride.

15. A method according to claim 1 or 2, wherein the monomer system comprises 1,4-diphenoxybenzene and terephthaloyl chloride.

16. A method according to claim 1 or 2, wherein the monomer system comprises 4,4'-diphenoxybenzophenone and phosgene or terephthaloyl chloride.

17. A method according to claim 1 or 2, wherein the monomer system comprises diphenyl ether and phosgene.

18. A method according to claim 1 or 2, wherein said monomer system comprises 1,4-diphenoxybenzene and phosgene.

19. A method according to claim 1 or 2, wherein a capping agent is added to the reaction medium.

20. A method according to claim 1 or 2, wherein both a nucleophilic and an electrophilic capping agent are added to the reaction medium.

21. A method according to claim 1 or 2, wherein the polymerisation is conducted at a tem-perature in the range from −30° C. to +25° C.

22. A method according to claim 1 or 2, wherein the controlling agent is selected to produce a dispersion of the oligomer.

* * * * *